United States Patent [19]

Spry

[11] Patent Number: 4,565,655

[45] Date of Patent: Jan. 21, 1986

[54] DIAZABICYCLONONENE ANTIBACTERIALS

[75] Inventor: Douglas O. Spry, Mooresville, Ind.

[73] Assignee: Eli Lilly and Company, Indianapolis, Ind.

[21] Appl. No.: 536,473

[22] Filed: Sep. 28, 1983

[51] Int. Cl.$^4$ ........................................... C07D 513/04
[52] U.S. Cl. ............................................. 260/245.2 R
[58] Field of Search ................................. 260/245.2 R

[56] References Cited

U.S. PATENT DOCUMENTS 4,064,343 12/1977 Chauvette .............................. 544/10

*Primary Examiner*—Mark L. Berch
*Attorney, Agent, or Firm*—William B. Scanlon; Arthur R. Whale

[57] ABSTRACT

Fused 4,7-β-lactam bicyclic antibacterials, namely 8-acylamino-4-anilino-9-oxo-6-thia-1,3-diazabicyclo[5.2.0]non-3-ene-2-carboxylic acids, and the esters, salts and sulfoxides thereof, are provided. The compounds as esters are prepared by process comprising heating a 3-azido-3-cephem ester with aniline, a substituted aniline, or an N-($C_1$–$C_3$ alkyl) derivative thereof.

6 Claims, No Drawings

DIAZABICYCLONONENE ANTIBACTERIALS

BACKGROUND OF THE INVENTION

This invention relates to antibacterial compounds. In particular, it relates to semi-synthetic β-lactam antibiotics which possess a 4,7-bicyclic ring system and to a process for the preparation thereof. The known β-lactam antibiotics, the penicillins and the cephalosporins, are fused bicyclic compounds possessing respectively the 4-membered β-lactam ring fused to the 5-membered thiazolidine ring and a 6-membered dihydrothiazine ring. Monocyclic β-lactams such as monobactam are known as are other bicyclic β-lactams such as thienomycin and the clavulanic acids.

The compounds provided by this invention structurally comprise a 4,7-bicyclic ring system having the 4-membered β-lactam ring fused to a 7-membered thiadiaza ring, formally designated as the 9-oxo-6-thia-1,3-diazabicyclo[5.2.0]non-3-ene bicyclic.

SUMMARY OF THE INVENTION

8-Acylamino-4-anilino-9-oxo-6-thia-1,3-diazabicyclo[5.2.0]non-3-ene-2-carboxylic acids, and salts thereof, are antibacterial agents which are obtained by the reaction of a 7-acylamino-3-azido-3-cephem-4-carboxylic acid ester with an aniline, or an N-alkyl aniline wherein the aniline ring is optionally substituted. The reaction results in the conversion of the 6-membered dihydrothiazine ring to the thiadiaza 7-membered ring. The 8-acyamino-4-anilinodiazabicyclonon-3-enes may be N-deacylated to form the correspondingly substituted 8-amino nucleus compound. The latter are useful intermediates for preparing 8-acylamino derivatives different from those directly obtainable by the reaction of the acylated azide with an aniline. Also provided are the esters and sulfoxides of the compounds.

DETAILED DESCRIPTION OF THE INVENTION

The bicyclic thiadiazanonene ring system of the compounds provided by this invention is represented by the following formula wherein the numbering system employed is indicated

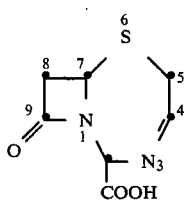

The compounds of the invention represented by the formula 1 below are substituted in the 4-position by an anilino substituent. As such, they possess an amidine structural moiety, one nitrogen of which is in the 7-membered ring and the other (aniline N) is not.

The compounds of the invention are named herein according to the ACS nomenclature system which uses the numbering system described above. However, for convenience, the cephalosporin compounds employed in the preparation of the compounds of the invention are named by the commonly used cepham nomenclature system rather than as 7-acylamino-8-oxo-5-thia-1-azabicyclo[4.2.0]oct-2-ene-2-carboxylic acids.

The compounds provided by this invention are represented by the following structural formula 1

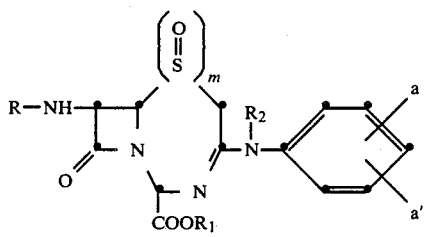

wherein R is hydrogen or an acyl group represented by the formula

wherein R' is hydrogen, $C_1$–$C_5$ alkyl, $C_1$–$C_5$ alkyl substituted by cyano or halogen; a phenyl or substituted phenyl group represented by the formula

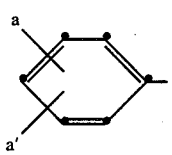

wherein a and a' independently are hydrogen, $C_1$–$C_4$ alkyl, $C_1$–$C_4$ alkoxy, halogen, hydroxy, amino, acetylamino, carboxy, carboxymethyl, or trifluoromethyl; a substituted methyl group represented by the formula $$R^1—Z)_nCH_2—$$

wherein $R^1$ is phenyl or substituted phenyl as defined above, cyclohex-1-ene, or cyclohexa-1,4-diene, Z is O or S, and n is 0 or 1; or R' is a heteroarylmethyl group represented by the formula

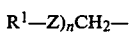

wherein $R^2$ is thienyl, furyl, tetrazolyl, thiazolyl, oxazolyl, isoxazolyl, thiadiazolyl, oxadiazolyl, wherein the heteroaryl group is optionally substituted by chloro, bromo, $C_1$–$C_4$ alkyl, amino, or protected amino; or R' is a disubstituted methyl group represented by the formula

wherein $R^3$ is $R^1$ and $R^2$, and Q is hydroxy, formyloxy, carboxy, amino, or sulfo; or R' is an oximino group represented by the formula

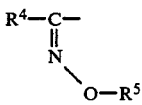

wherein $R^4$ is $R^1$ and $R^2$, and $R^5$ is $C_1$–$C_4$ alkyl, carboxy-substituted $C_1$–$C_7$ alkyl, or carboxy-substituted $C_3$–$C_7$ cycloalkyl;

$R_2$ is hydrogen or $C_1$–$C_3$ alkyl, and a and a' have the same meanings as defined hereinabove;

m is 0 or 1;

$R_1$ is hydrogen or a carboxy-protecting group and when $R_1$ is hydrogen, the pharmaceutically acceptable non-toxic salts thereof.

In the foregoing definition of the compounds of the invention, $C_1$–$C_5$ alkyl refers to methyl, ethyl, n-propyl, isopropyl, n-butyl, t-butyl, n-amyl, isoamyl, and like straight and branched chain hydrocarbon radicals; $C_1$–$C_5$ alkyl substituted by cyano or halogen, refers to cyanomethyl, 2-cyanoethyl, 3-cyanopropyl, 2-cyanopropyl, chloromethyl, bromomethyl, 2-chloroethyl, 4-chlorobutyl, 5-bromoamyl, and the like; $C_1$–$C_4$ alkoxy refers to methoxy, ethoxy, n-propoxy, isopropoxy, n-butoxy, t-butoxy, and the like; and halogen refers to fluoro, chloro, bromo, and iodo.

When in the formula 1, R' is a heteroarylmethyl group, $R^2$—$CH_2$— wherein the heteroaryl group may be substituted by chloro, bromo, $C_1$–$C_4$ alkyl, amino, or protected amino, examples of such substituted groups are 4-methyl-2-thienyl, 3-chloro-2-thienyl, 3-amino-2-thienyl, 4-methyl-2-furyl, 3-chloro-2-furyl, 1-methyltetrazol-5-yl, 5-methyltetrazol-1-yl, 5-bromotetrazol-1-yl, 2-aminothiazol-4-yl, 2-aminooxazol-4-yl, 5-amino-1,3,4-thiadiazol-2-yl, 5-chloro-1,3,4-thiadiazol-2-yl, 5-methyl-1,3,4-thiadiazol-2-yl, 5-methylisoxazol-4-yl, 3-amino-1,2,4-thiadiazol-5-yl, 3-amino-1,2,4-oxadiazol-5-yl, 3-methyl-1,2,4-thiadiazol-5-yl, 3-tritylamino-1,2,4-thiadiazol-5-yl, and like substituted heteroaryl groups.

Examples of disubstituted methyl groups, $R^3$—CH(-Q)—, in the above formula 1 are (phenyl)aminomethyl, (4-hydroxyphenyl)aminomethyl, (3-chloro-4-hydroxyphenyl)aminomethyl, (2-thienyl)aminomethyl, (3-thienyl)aminomethyl, (1,4-cyclohexadien-1-yl)aminomethyl, (2-aminothiazol-4-yl)aminomethyl, (4-chloroisoxazol-3-yl)aminomethyl, (2-methyl-1,3,4-thiadiazol-5-yl)aminomethyl, (phenyl)hydroxymethyl, (phenyl)carboxymethyl, (2-thienyl)carboxymethyl, (3-thienyl)carboxymethyl, (phenyl)sulfomethyl, (tetrazol-1-yl)aminomethyl, (2-aminothiazol-4-yl)hydroxymethyl, (4-hydroxyphenyl)caboxymethyl, and like groups.

When in the formula 1 R' is an oximino group $R^4$—C(=N—$OR^5$)— representative carboxy-substituted $C_1$–$C_4$ alkyl group, $R^5$, are carboxymethyl, 2-carboxyethyl, 1-carboxyethyl, 2-carboxyprop-2-yl, 4-carboxybutyl, 3-carboxypentyl, 3-carboxyhexyl, and like groups. When $R^5$ is a carboxy-substituted alkyl group examples of such include 1-carboxycyclobut-1-yl, 1-carboxycycloprop-1-yl, 1-carboxycyclopent-1-yl, and the like. Examples of $R^4$ groups of the oximino group include, phenyl, 2-furyl, 2-thienyl, 2-aminothiazol-4-yl, 2-aminooxazol-4-yl, 3-amino-1,2,4-thiadiazol-5-yl, 3-amino-1,2,4-oxadiazol-5-yl, 5-methyl-1,3,4-thiadiazol-2-yl, 5-methyl-1,3,4-oxadiazol-2-yl, and like groups.

The term "protected amino" as used herein and in the definition of formula 1 compounds refers to the amino group substituted with an art recognized protecting or blocking group. Examples of such groups are trityl, acetyl, chloroacetyl, t-butyloxycarbonyl, cyclopentyloxycarbonyl, adamantyloxycarbonyl, ethoxycarbonyl, or enamines formed with the amine and β-keto esters such as ethyl or methyl acetoacetate, and like known amino protecting groups. Likewise, the term carboxy protecting group (R1) refers to an art recognized carboxylic acid protecting ester group such as, for example, an alkyl, substituted alkyl, benzyl, or substituted benzyl group. Examples of such ester forming groups commonly employed for the temporary protection of the carboxy group are t-butyl, allyl, 2-iodoethyl, methoxyethyl, 2,2,2-trichloroethyl, dimethylvinylcarbinyl, benzyl, 4-nitrobenzyl, 4-methoxybenzyl, diphenylmethyl, and like ester groups which are readily cleavable under hydrolytic or hydrogenolytic conditions.

The compounds represented by the formula 1 when $R_1$ is hydrogen, form salts with suitable bases. Examples of such salts are the sodium, potassium, ammonium, calcium and like salts. Preferred salts are formed with pharmaceutically acceptable bases of which a wide variety are known. Examples include the salts formed with the hydroxyalkylamines such as di-(2-hydroxyethyl)amine, 2-hydroxyethylamine, 3-hydroxypropylamine, dicyclohexylamine, cyclohexylamine, diethylamine, procaine, and like amines. Such salts can be used to prepare pharmaceutical formulations of the compounds of the invention.

The compounds of the formula 1 are prepared by the process of this invention which comprises reacting a 3-azido-3-cephem ester represented by the formula 2

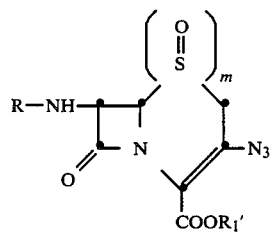

wherein R has the same meanings as defined for formula 1, $R_1'$ is a carboxy protecting group, and m is 0 or 1; with an aniline represented by the formula

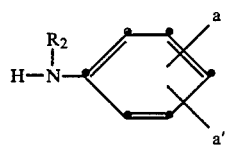

wherein $R_2$, a, and a' have the same meanings as defined for formula 1. The reaction is carried out in an inert solvent at a temperature between about 45° C. and about 95° C. An excess of the aniline is preferably used in the reaction process and, in general a 2–3 molar excess is suitable. The reaction product is recovered from the reaction product mixture and separated from the excess aniline and other side products. In general, the reaction mixture is evaporated to dryness and the crude product is purified by chromatography over silica gel or other suitable chromatographic material. The crude reaction product may also be slurried in an organic solvent such as acetone to remove the excess aniline the slurry filtered, the filtrate evaporated, and the reaction product purified by crystallization or by chromatography. Alternatively the reaction product as the crude ester may be deesterified to the free acid (formula 1, $R_1$=H) and the acid purified, either as such, or in the form of a salt.

Solvents which can be used in the reaction process are inert to the 3-azido ester (2) and the aniline. Ketones such as acetone, and methylethylketone, and esters such as ethyl or methyl acetate or iso-amyl acetate are suitable solvents. Halogenated hydrocarbons such as methylene chloride and trichloroethane may also be used.

An example of the preparation of the compounds of the invention comprises reacting p-nitrobenzyl 7β-(2-thienylacetylamino)-3-azido-3-cephem-4-carboxylate in acetone at the reflux temperature with N-methylaniline to provide the compound represented by the formula 1 wherein R is 2-thienylacetyl, $R_1$ is p-nitrobenzyl, $R_2$ is methyl, and a and a' are both hydrogen.

Anilines which are used in the preparation of formula 1 compounds are exemplified by aniline, N-methylaniline, 4-chloroaniline, 3-trifluoromethylaniline, N-ethylaniline, 2-chloroaniline, 4-methylaniline, N-methyl-4-ethylaniline, N-(n-propyl)aniline, 2-fluoroaniline, 3-fluoroaniline, 3-ethoxyaniline, N-methyl-4-methoxyaniline, 3,4-dichloro-N-methylaniline, 2,4-dimethyl-N-methylaniline, 4-t-butyl N-methylaniline, and like anilines.

The 3-azido-3-cephem esters represented by the formula 2 are prepared with a correspondingly substituted 3-halo-3-cephem ester or a 3-sulfonyloxy-3-cephem ester or the sulfoxides thereof and sodium azide. The preparation is carried out by mixing the 3-halo or 3-sulfonyloxy compound in an inert solvent such as dimethylformamide with excess sodium azide and stirring the mixture at a temperature between about 5° C. and 25° C. The 3-azido-3-cephem ester is recovered from the reaction mixture by diluting the mixture with an organic solvent such as ethyl acetate, washing the organic mixture with water and brine, drying the organic solution, and evaporating the dried solution to obtain the 3-azido-3-cephem ester. The ester can be further purified by crystallization or by chromatography.

The compounds represented by the formula 1 wherein R is an acyl group and $R_1$ is hydrogen and the pharmaceutically acceptable non-toxic salts thereof inhibit the growth of microorganisms pathogenic to man and animals. The salts, for example the sodium of potassium salts, can be formulated in aqueous solution and used as antibacterial agents by topical application to skin. Such solutions may also be applied to cuts and abrasions to sterilize and control infections. It may also be desirable to administer the salts parenterally or orally for treatment of infections caused by staphylococcus and streptococcus as well as other infectious microorganisms.

The compounds of the formula 1 in esterified form ($R_1$ = carboxy protecting group) are useful as intermediates for preparing compounds wherein $R_1$ is H or a salt.

The compounds of the formula 1 wherein R is hydrogen are also useful as intermediates. For example, the 7-position acylamino group of the 3-azido-3-cephem ester may not be the acylamino group at the 8-position of the desired 4-anilinodiazabicyclononene after reaction with the aniline. In this instance, the acylamino group at the 8-position of the bicyclononene product may be N-deacylated by known procedures to provide the compound of claim 1 wherein R is hydrogen. The 8-amino-4-anilinodiazabicyclononene ester then can be reacylated with the desired carboxylic acid to form the desired acylamino substituent at the 8-position.

The 8-amino-4-anilinodiazabicyclononene nucleus compound is obtained by reacting the 8-acylamino derivative with an imino halide forming reagent such as a phosphorus halide eg. phosphorus pentachloride, in an inert solvent. The imino halide (formed at the 8-position amido group) is converted to the corresponding enol ether by the addition of an alcohol or diol such as methyl alcohol or propane-1,3-diol, and the enol ether is decomposed by hydrolysis to provide the 8-amino nucleus compound. The 3-step reaction can be carried out in a halogenated hydrocarbon solvent such as methylene chloride or trichloroethane. The process is carried out at cold temperatures of about −5° C. to about 10° C. In an example of the process, 2R-(2α,7α,8β)-4-(N-methylanilino)-9-oxo-8-[(phenoxyacetyl)amino]-6-thia-1,3-diazabicyclo[5.2.0]non-3-en-2-carboxylic acid 4-nitrobenzyl ester is reacted at about 0° C. in methylene chloride with phosphorus pentachloride. Methyl alcohol is then added to the cold mixture which is then allowed to warm to 15° C. to 20° C. The imino ether formed is then hydrolyzed by adding water to the reaction mixture. The 8-amino nucleus compound is recovered from the reaction mixture, preferably in the form of the dihydrochloride salt.

The 8-amino nucleus intermediate is reacylated by following the known procedures used for acylating the penicillin nucleus (6APA) and the cephalosporin nuclei eg. 7ACA and 7ADCA. The acylation can be carried out under aqueous or non-aqueous conditions by employing an activated derivative of the acyl forming carboxylic acid. Derivatives such as the acid halides, acid azides, anhydrides and active esters may be used in the acylation. For example, the 8-amino-4-anilinobicyclononene ester is reacted with 2-(2-tritylaminothiazol-4-yl)-2-methoxyiminoacetyl chloride to provide the amino-protected ester. Deesterification of the ester protecting group and removal of the trityl group provides the desired compound represented by the following formula.

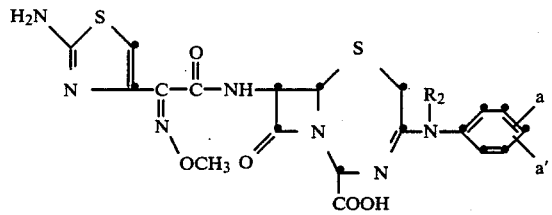

The compounds of the formula 1 wherein m is 1, the sulfoxide form, are intermediates prepared with the 3-azido-3-cephem ester sulfoxides (formula 2, n=1) and the aniline as described hereinabove. The use of the 3-azido-3-cephem sulfoxide prevents an undue amount of isomerization of the 3-cephem to a 2-cephem both during the preparation of the 3-azido starting material as well as during the reaction of the 3-azido-3-cephem with an aniline. The latter isomerization results in the formation of side products. The sulfoxides of the formula 1 may also be useful in the isolation of the compounds since sulfoxides generally can impart greater crystallinity and less solubility.

The sulfoxide form of the azide is prepared by known methods, eg. by oxidizing the sulfide form with a peracid eg. m-chloroperbenzoic acid.

Following the preparation of a compound of the invention as the sulfoxide (formula 1, m=1) the sulfoxide is reduced to the sulfide (m=0) by known sulfoxide reducing methods. One such method is that described by Hatfield, U.S. Pat. No. 4,044,002 employing acetyl bromide and amylene.

The following examples further describe the present invention.

Preparations of 3-azido-3-cephem esters.

PREPARATION 1

Allyl 7β-(2-thienylacetamido)-3-azido-3-cephem-4-carboxylate

To a solution of 0.409 g. of allyl 7β-(2-thienylacetamido)-3-chloro-3-cephem-4-carboxylate in 20 ml. of dimethylformanide cooled to about 5° C. in an ice bath were added 0.073 g. (1.1 eg.) of sodium azide. The reaction mixture was stirred in the cold for 1.5 hr. and then was transferred to a separatory funnel with cold ethyl acetate. The mixture was washed five times with water, once with brine, dried over sodium sulfate and evaporated to dryness in vacuo at 30° C. There were obtained 0.389 g. (94%) of the 3-azido compound.

IR (chloroform): 2100 and 1780 cm$^{-1}$.

NMR (T-60, CDCl$_3$): δ3.58 (s, 2H, C$_2$—H), 3.38 (s, 2H, side chain CH$_2$), 4.72 (m, 2H, allyl CH$_2$), 4.93 (d J=4 Hz, 1H, C$_6$—H), 5.2–5.6 (m, 3H, allyl), 5.75 (d, d J=4, 8 Hz, 1H, C$_7$—H), and 7.50 (d, 1H, NH).

PREPARATION 2 p-Nitrobenzyl 7β-(2-thienylacetamido)-3-azido-3-cephem-4-carboxylate

To a solution of 0.554 g. of p-nitrobenzyl 7β-(2-thienylacetamido-3-methylsulfonyloxy-3-cephem-4-carboxylate in 10 ml. of DMF was added one molar equivalent (0.065 g.) of sodium azide and the mixture stirred at room temperature for 30 minutes. The mixture was transferred to a separatory funnel with ethyl acetate and the solution was washed three times with water, once with brine, dried over sodium sulfate and evaporated to dryness. The product, 0.523 g. obtained as a yellow froth showed a single spot on silica gel thin layer chromatography using 1:1, ethyl acetate:toluene for development and iodine for visualization.

PREPARATION 3

Methyl 7β-(2-thienylacetamido)-3-azido-3-cephem-4-carboxylate

A twenty gram mixture of methyl 7β-(2-thienylacetamido)-3-chloro-3-cephem-4-carboxylate and the corresponding 2-cephem isomer was dissolved in 100 ml. of DMF, the solution cooled to about 5° C. in an ice bath, and 1.1 eg. (3.84 g.) of sodium azide were added. The reaction mixture was stirred at 5° C. for 30 minutes and for one hour without cooling. The reaction mixture was transferred to a separatory funnel with ethyl acetate and washed five times with water, once with brine, dried and evaporated to dryness to yield 19.5 g. of crude product as a brown solid.

IR (CHCl$_3$): 2100 cm$^{-1}$ (azide), 1770 cm$^{-1}$ (β-lactam carbonyl).

U.V. λmax 296 nm ε=8,000 (ethanol).

NMR (T60, CDCl$_3$): δ3.57 (br. s, 2H, C$_2$—H), 3.87 (s, 2H, side chain methylene), 4.97 (d, J=4 Hz, 1H, C$_6$—H), 5.70 (d, d J=4, 8 Hz, 1H, C$_7$—H).

PREPARATION 4

Diphenylmethyl 7β-phenoxyacetamido-3-azido-3-cephem-4-carboxylate

To a solution of 1.728 g. of diphenylmethyl 7β-phenoxyacetamido-3-chloro-3-cephem-4-carboxylate in 25 ml. of DMF were added 1.05 eg. (0.220 g.) of sodium azide and the mixture was stirred at room temperature for one hour. The reaction mixture was transferred to a separatory funnel with ethyl acetate and washed three times with water, once with brine, dried, and evaporated to dryness. The crude product was purified by chromatography over 15 g. of silica gel using 500 ml. of toluene vs. 500 l. of 1:1 ethylacetate:toluene for elution. Multiple fractions were collected with fractions 24 to 31 being combined. The pooled fractions were evaporated to dryness to yield 0.795 g. of product as a yellow froth.

IR (CHCl$_3$) 2105 cm$^{-1}$, 1785 cm$^{-1}$.

NMR (CDCL$_3$) δ2.80, 3.27 (ABq J=16 Hz, 2H, C$_2$—H), 4.57 (s, 2H, side chain CH$_2$), 4.92 (d, J=4 Hz, 1H, C$_6$—H, 5.60 (d, d J=4, 8 Hz, C$_7$—H).

PREPARATION 5

2,2,2-Trichloroethyl 7β-(2-thienylacetamido)-3-azido-3-cephem-4-carboxylate

To a solution of 2.926 g. of 2,2,2-trichloroethyl 7β-(2-thienylacetamido)-3-chloro-3-cephem-4-carboxylate in 17 ml. of DMF was cooled to 5° C. in an ice bath and 0.427 g. of sodium azide were added. The reaction mixture was stirred in an ice bath for 2 hr. and was then transferred to a separatory funnel with ethyl acetate. The mixture was washed with water and brine, dried and evaporated to dryness. There were obtained 2.54 g. of the crude 3-azido product.

IR (CHCl$_3$) 2110, 1788 cm$^{-1}$.

UV λmax 300 nm ε=3,800 (ethanol).

NMR (T-60, CDCl$_3$): δ3.58 (s, 2H, C$_2$—H, 3.85 (s, 2H, side chain CH$_2$), 4.75, 4.98 (ABq J=11 Hz, 2H, ester), 5.00 (d, J=4 Hz, 1H, C$_6$—H), 5.73 (d, d J=4, 8 Hz, 1H, C$_7$—H).

PREPARATION 6

Methyl 7β-acetamido-3-azido-3-cephem-4-carboxylate

A solution of 0.784 g. of methyl 7β-acetamido-3-chloro-3-cephem-4-carboxylate in 40 ml. of DMF was cooled to 5° C. in an ice bath and 0.193 g. of sodium azide were added. The reaction mixture was stirred in the cold for 45 minutes and then transferred to a separatory funnel with ethyl acetate. The mixture was washed with cold water, with brine, and was dried and evaporated to dryness. There were obtained 0.581 g. of the 3-azido ester product as a yellow solid.

EXAMPLE 1

2R-(2α,7α,8β)-4-(N-Methylanilino)-9-oxo-8-[(2-thienylacetyl)amino]-6-thia-1,3-diazabicyclo[5.2.0]non-3-ene-2-carboxylic acid sodium salt To a solution of 0.622 g of 4-nitrobenzyl 7β-(2-thienylacetylamino)-3-azido-3-cephem-4-carboxylate in 40 ml of acetone were added 3.0 equivalents (0.40 ml) of N-methylaniline and the solution was heated at the reflux temperature for one hour. The reaction mixture was evaporated to dryness at about 57° C. and further evaporated under vacuum (pump) to provide the crude reaction product as a solid. The solid was slurried with acetone and filtered to provide 0.149 g (20.7% yield) of the title compound as the 4-nitrobenzyl ester as a white solid.

FDMS 579

NMR (270 MHz, DMSOd$_6$) δ 3.20 (s, 3H, N—CH$_3$), 3.34 (s, 2H, C$_5$H), 3.75 (s, 2H, side chain CH$_2$), 5.3–5.5 (m, 4H, C$_7$H+C$_8$H+pNB), 6.16 (s, 1H, C$_2$H), 9.14 (d J=8 Hz, NH).

The ester was deesterified as follows. The ester was dissolved in 25 ml. of warm dimethylsulfoxide and 20 ml of ethyl acetate and a solution of 0.072 g of sodium bicarbonate in 5 ml of water was added. The mixture was hydrogenated in a Parr hydrogenation apparatus over 0.247 g of 5% Pd/c under 50 psihydrogen pressure for one hour. The reduction mixture was filtered and the filtrate lyophilized to a solid. The solid was dissolved in water, refiltered, and lyophilized to provide the title compound as a solid.

The title compound inhibited the growth of a number of pathogenic microorganisms in the Disc-Plate in vitro test. The activity was demonstrated by the size of the zones of inhibition (mm of diameter of zone). The concentration of the title compound was 1 mg/ml. The following are the organisms, with the zone size in parenthesis, controlled by the title compound: *Staphylococcus aureus* (21), *Bacillus subtilis* (16), *Bacillus subtilis* grown on minimal medium (24), *Bacillus stearothyermophilus* (11), *Micrococcus luteus* (13), *Escherichia coli* (15), *Pseudomonas solanacearum* (no zone at 1 mg/ml., a 10 mm zone at 5 mg/ml.

EXAMPLE 2

2R-(2α,7α,8β)-4-anilino-9-oxo-8-[(2-thienylacetyl)amino]-6-thia-1,3-diazabicyclo[5.2.0]non-3-ene-2-carboxylic acid sodium salt To a solution of 0.551 g of p-nitrobenzyl 7β-(2-thienylacetylamino)-3-azido-3-cephem-4-carboxylate in 40 ml of acetone was added a solution of 0.308 g of aniline in 50 ml of acetone and the mixture was heated at the reflux temperature for one hour. The reaction mixture was evaporated to dryness and the crude reaction product mixture chromatographed on 8.0 g of silica gel packed in toluene using 400 ml of 10% ethyl acetate in toluene (v:v) vs 400 ml of ethyl acetate. Multiple fractions were collected and all fractions containing the same product (via tlc) were combined and evaporated. There were obtained 0.08 g of the title compound as the p-nitrobenzyl ester.

MS (field desorption) 565, 474, 378, 375.

IR (chloroform) 1780 cm$^{-1}$ (β-lactam carbonyl).

UV (C$_2$H$_5$OH) λmax 235 nm ε 17,000. λmax 265 nm ε 14,000.

There were also obtained 0.053 g of p-nitrobenzyl 7β-(2-thienylacetylamino)-2-anilino-3-amino-3-cephem-4-carboxylate as side product.

The title compound is obtained by deesterifying the p-nitrobenzyl ester by the hydrogenation procedure described by Example 1.

I claim:

1. The process for preparing a compound of the formula

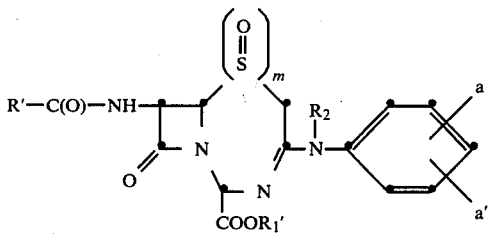

wherein R' is hydrogen, C$_1$–C$_5$ alkyl, C$_1$–C$_5$ alkyl substituted by cyano or halogen;

a phenyl or a substituted phenyl group represented by the formula

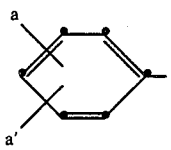

wherein a and a' independently are hydrogen, C$_1$–C$_4$ alkyl, C$_1$–C$_4$ alkoxy, halogen, hydroxy, amino, acetylamino, carboxy, carboxymethyl, or trifluoromethyl;

a substituted methyl group of the formula

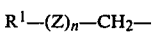

wherein R$^1$ is phenyl, substituted phenyl as defined above, cyclohex-1-ene or cyclohexa-1,4-diene, Z is O or S, and n is 0 or 1; a heteroarylmethyl group of the formula

wherein R$^2$ is thienyl, furyl, tetrazolyl, thiazolyl, oxazolyl, isoxazolyl, thiadiazolyl, oxadiazolyl, wherein said hetero ring is optionally substituted by chloro, bromo, C$_1$–C$_4$ alkyl, amino, or protected amino;

a disubstituted methyl group of the formula

wherein R$^3$ is R$^1$ or R$^2$ as defined above, and Q is hydroxy, formyloxy, carboxy, amino, or sulfo;

an oximino group of the formula

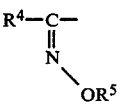

wherein

R$^4$ is R$^1$ or R$^2$ as defined above and R$^5$ is C$_1$–C$_4$ alkyl, monocarboxy-substituted C$_1$–C$_7$ alkyl, or monocarboxy-substituted C$_3$–C$_7$ cycloalkyl;

R$_2$ is hydrogen or C$_1$–C$_3$ alkyl;

m is 0 or 1; and

R$_1$' is a carboxy protecting group;

which comprises heating in an inert solvent at a temperature between about 45° C. and about 95° C. a 3-azido-3-cephem ester of the formula

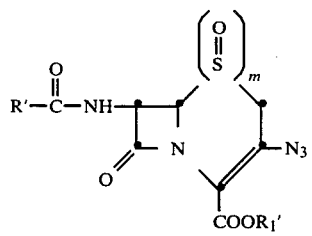

wherein R', $R_1'$ and m have the same meanings as defined above; with an aniline of the formula

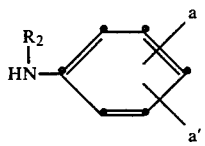

wherein $R_2$, a and a' have the same meanings as defined above.

2. The process of claim 1 wherein m is 0.
3. The process of claim 1 wherein $R_1'$ is 4-nitrobenzyl, 4-methoxybenzyl, or diphenylmethyl.
4. The process of claim 1 wherein $R_2$ is $C_1$-$C_3$ alkyl.
5. The process of claim 4 wherein R' is a group of the formula $R^2$—$CH_2$—.
6. The process of claim 4 wherein R' is a group of the formula

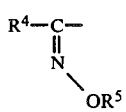

and $R^5$ is $C_1$-$C_4$ alkyl.